US012630543B2

(12) United States Patent
Seino et al.

(10) Patent No.: US 12,630,543 B2
(45) Date of Patent: May 19, 2026

(54) FLUORINE-CONTAINING PYRAZOLE COMPOUND AND METHOD FOR PRODUCING SAME

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 981 days.

(21) Appl. No.: 17/768,884

(22) PCT Filed: Oct. 30, 2020

(86) PCT No.: PCT/JP2020/040923

§ 371 (c)(1),
(2) Date: Apr. 14, 2022

(87) PCT Pub. No.: WO2021/095577

PCT Pub. Date: May 20, 2021

(65) Prior Publication Data

US 2024/0116915 A1 Apr. 11, 2024

(30) Foreign Application Priority Data

Nov. 14, 2019 (JP) ................................ 2019-206403

(51) Int. Cl.

*C07D 401/04* (2006.01)
*A01N 43/56* (2006.01)
*A01N 43/78* (2006.01)
*A01P 1/00* (2006.01)
*C07D 417/04* (2006.01)

(52) U.S. Cl.

CPC .............. *C07D 417/04* (2013.01); *A01P 1/00* (2021.08); *C07D 401/04* (2013.01)

(58) Field of Classification Search

CPC .... C07D 401/04; C07D 417/04; A01N 43/56; A01P 1/00

See application file for complete search history.

(56) References Cited

U.S. PATENT DOCUMENTS

| | | | |
|---|---|---|---|
| 2004/0072692 | A1 | 4/2004 | Hoffmann et al. |
| 2005/0038041 | A1 | 2/2005 | Nakagawa et al. |
| 2006/0122063 | A1 | 6/2006 | Hoffmann et al. |
| 2009/0042917 | A1 | 2/2009 | Bessho et al. |
| 2011/0301181 | A1 | 12/2011 | Maue et al. |
| 2015/0099766 | A1 | 4/2015 | Maue et al. |
| 2015/0166564 | A1 | 6/2015 | Allen et al. |
| 2016/0289213 | A1 | 10/2016 | Pazenok et al. |
| 2017/0217936 | A1 | 8/2017 | Allen et al. |
| 2018/0334450 | A1 | 11/2018 | Allen et al. |
| 2019/0359597 | A1 | 11/2019 | Allen et al. |

FOREIGN PATENT DOCUMENTS

| | | | | |
|---|---|---|---|---|
| CN | 1671702 | A | 9/2005 | |
| CN | 102317263 | A | 1/2012 | |
| CN | 103649076 | A | 3/2014 | |
| CN | 105934428 | A | 9/2016 | |
| JP | H05-230029 | A | 9/1993 | |
| JP | 2006-504662 | A | 2/2006 | |
| JP | 2012-507482 | A | 3/2012 | |
| JP | 2014-514360 | A | 6/2014 | |
| JP | 2016-539945 | A | 12/2016 | |
| WO | WO-2015041360 | A1 * | 3/2015 | ........... A01N 43/713 |
| WO | 2019-141957 | A1 | 7/2019 | |

OTHER PUBLICATIONS

English translation of WIPO Publication WO-2015041360-A1, retrieved on Feb. 20, 2025. https://patents.google.com/patent/WO2015041360A1/en?oq=wo2015041360. (Year: 2025).*

Clark, "Halogens as oxidising agents", https://www.chemguide.co.uk/inorganic/group7/halogensasoas.html, last modified in May 2015. retrieved on May 13, 2020. (Year: 2015).*

Notice of Reasons for Refusal issued in corresponding Japanese Patent Application No. 2021-556024 dated Apr. 4, 2023, with English translation (8 Pages).

First Office Action issued in corresponding Chinese Patent Application No. 202080071466.4 dated Nov. 1, 2023, with English translation (31 Pages).

M. D. Bargamova et al., "5-Fluorosubstituted Pyrazoles", Plenum Publishing Corporation, 1991, pp. 2338-2344 (7 Pages).

Wei Wang, et al., "Synthesis and Insecticidal Evaluation of Novel N-pyridylpyrazole Derivatives Containing Diacylhydrazine/1,3,4-Oxadiazole Moieties", Journal of Heterocyclic Chemistry, vol. 56, Issue 4, Jan. 22, 2019, pp. 1330-1336.

(Continued)

*Primary Examiner* — Kamal A Saeed
*Assistant Examiner* — Sagar Patel
(74) *Attorney, Agent, or Firm* — Harness, Dickey & Pierce, P.L.C.

(57) ABSTRACT

A fluorine-containing pyrazole compound is represented by the following general formula (1):

[Formula 1]

(1)

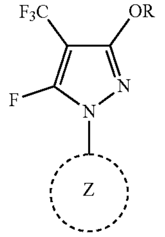

wherein in formula (1) above, R represents a hydrocarbon group having 1 to 12 carbon atoms, and a ring Z represents an aromatic heterocyclic ring containing at least one heteroatom selected from the group consisting of a nitrogen atom, an oxygen atom, and a sulfur atom.

11 Claims, No Drawings

(56) References Cited

OTHER PUBLICATIONS

Seok Jong Kang et al., "Synthesis and Anti-Tumor Activity of Imidazopyrazines as TAK1 Inhibitors", European Journal of Medicinal Chemistry, vol. 163, Feb. 1, 2019, pp. 660-670.

International Search Report for corresponding International Application No. PCT/JP2020/040923 dated Jan. 12, 2021 (11 Pages).

Bargamova, M.A. et al., "5-Fluoro-sullstitutecl Pyrazoles, Izvestiya Akademii Nauk SSSR", Seriya Khimicheskaya, 1990, (11), pp. 2583-2589, ISSN:0002-3353, p. 2583, Compound (IV)—Cited in International Search Report and Written Opinion.

Written Opinion for corresponding International Application No. PCT/JP2020/040923 dated Jan. 12, 2021, with English translation (8 Pages).

International Preliminary Report on Patentability for corresponding International Application No. PCT/JP2020/040923 dated Jan. 12, 2021, with English translation (9 Pages).

Decision of Refusal issued in corresponding Japanese Patent Application No. 2021-556024 dated Aug. 15, 2023, with English translation (10 Pages).

Extended European Search Report issued in corresponding European Patent Application No. 20887812.4 dated Sep. 5, 2023 (7 Pages).

Office Action for corresponding Indian Application No. 202237027395 dated Feb. 9, 2023, with English translation (6 Pages).

* cited by examiner

FLUORINE-CONTAINING PYRAZOLE COMPOUND AND METHOD FOR PRODUCING SAME

CROSS REFERENCE TO RELATED APPLICATIONS

The present application is a national stage application of International Patent Application No. PCT/JP2020/040923 filed on Oct. 30, 2020, which claims the benefit of Japanese Patent Application No. 2019-206403, filed on Nov. 14, 2019. The contents of both the above applications are hereby incorporated by reference herein in their entireties.

BACKGROUND

Technical Field

The present disclosure relates to a fluorine-containing pyrazole compound and a method for producing the same.

Related Art

Conventionally, fluorine-containing pyrazole compounds have been reported to have various biological activities. Among them, a compound having a heterocyclic ring as a substituent at the 1-position of a pyrazole ring and substituents at the 3- and 5-positions of the pyrazole ring is expected to be used in the fields of medicine and agrochemicals.

More specifically, Journal of Heterocyclic Chemistry, Vol. 56, 2019, pp. 1330 to 1336 reports that a compound having a 1-(2-pyridyl)-pyrazole structure has an insecticidal activity of armyworm and diamondback moth. European Journal of Medicinal Chemistry, Volume 163, 2019, pp. 660 to 670 reports that a compound having a 1-(3-pyridyl)-pyrazole structure has an inhibitory activity on a stress response kinase (Transforming growth factor beta-activated kinase 1 (TAK1)).

Therefore, with an expectation of improving useful activities such as biological activity, a compound having a substituent of heterocyclic ring at the 1-position of a pyrazole ring and substituents at the 3- and 5-positions of the pyrazole ring, and further a trifluoromethyl group at the 4-position of the pyrazole ring, has been drawn attraction in development thereof.

Technical Problem

For the compound having a substituent of heterocyclic ring at the 1-position of the pyrazole ring and substituents at the 3- and 5-positions of the pyrazole ring, reactivity and reaction selectivity of a substrate need to be strictly controlled in order to further introduce a trifluoromethyl group at the 4-position of the pyrazole ring, and no production examples of such a compound have been reported so far. Therefore, a fluorine-containing pyrazole compound having a substituent of heterocyclic ring at the 1-position, substituents at the 3- and 5-positions, and further a trifluoromethyl group at the 4-position has been waited for further development.

Therefore, the present inventors have discovered that a reaction with a specific raw material enables introduction of a heterocyclic structure at the 1-position of a pyrazole ring, a trifluoromethyl group at the 4-position of a pyrazole ring, and specific substituents at the 3-position and the 5-position of a pyrazole ring, and thus have completed the present disclosure. Namely, the present disclosure provides a novel fluorine-containing pyrazole compound having a heterocyclic structure at the 1-position, a trifluoromethyl group at the 4-position, and specific substituents at the 3-position and the 5-position, which have not been known conventionally, and a method capable of easily producing the fluorine-containing pyrazole compound.

SUMMARY

The configuration of the present disclosure is as follows.

[1] A fluorine-containing pyrazole compound represented by the following general formula (1):

[Formula 1]

(1)

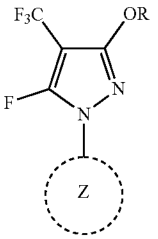

wherein R represents a hydrocarbon group having 1 to 12 carbon atoms; and a ring Z represents an aromatic heterocyclic ring containing at least one heteroatom selected from the group consisting of a nitrogen atom, an oxygen atom, and a sulfur atom.

[2] The fluorine-containing pyrazole compound according to [1], wherein a number of π electrons constituting the ring Z is 6, 10, or 14.

[3] The fluorine-containing pyrazole compound according to [1], wherein the ring Z contains at least a nitrogen atom as the heteroatom, and a number of π electrons constituting the ring Z is 6 or 10.

[4] A method for producing a fluorine-containing pyrazole compound, including reacting a fluoroisobutylene derivative represented by the following general formula (2) with a compound represented by the following general formula (3) or a salt thereof to obtain a fluorine-containing pyrazole compound represented by the following general formula (1):

[Formula 2]

(2)

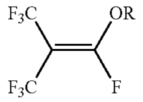

(3)

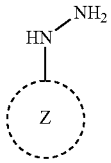

-continued (1)

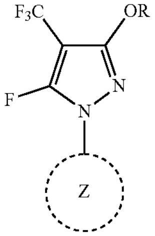

wherein

R represents a hydrocarbon group having 1 to 12 carbon atoms, and a ring Z represents an aromatic heterocyclic ring containing at least one heteroatom selected from the group consisting of a nitrogen atom, an oxygen atom, and a sulfur atom.

[5] A method for producing a fluorine-containing pyrazole compound, including reacting a fluoroisobutane derivative represented by the following general formula (4) with a compound represented by the following general formula (3) or a salt thereof to obtain a fluorine-containing pyrazole compound represented by the following general formula (1):

[Formula 3]

(4)

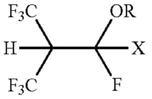

(3)

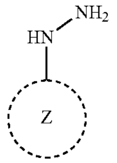

(1)

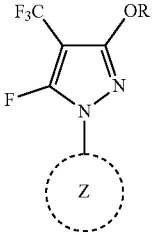

wherein

R represents a hydrocarbon group having 1 to 12 carbon atoms,

X represents a halogen atom, —$OA^1$, —$SO_mA^1$ where m is an integer of 0 to 3, or —$NA^1A^2$, $A^1$ and $A^2$ each independently represent a hydrogen atom or a hydrocarbon group having 1 to 10 carbon atoms, and a ring Z represents an aromatic heterocyclic ring containing at least one heteroatom selected from the group consisting of a nitrogen atom, an oxygen atom, and a sulfur atom.

[6] The method for producing a fluorine-containing pyrazole compound according to [4], wherein a step of obtaining a fluorine-containing pyrazole compound is carried out in the presence of a fluoride ion scavenger.

[7] The method for producing a fluorine-containing pyrazole compound according to [4], wherein a number of π electrons constituting the ring Z is 6, 10, or 14.

[8] The method for producing a fluorine-containing pyrazole compound according to [4], wherein the ring Z contains at least a nitrogen atom as the heteroatom, and a number of π electrons constituting the ring Z is 6 or 10.

[9] The method for producing a fluorine-containing pyrazole compound according to [5], wherein a step of obtaining a fluorine-containing pyrazole compound is carried out in the presence of a fluoride ion scavenger.

[10] The method for producing a fluorine-containing pyrazole compound according to [5], wherein a number of π electrons constituting the ring Z is 6, 10, or 14.

[11] The method for producing a fluorine-containing pyrazole compound according to [5], wherein the ring Z contains at least a nitrogen atom as the heteroatom, and a number of π electrons constituting the ring Z is 6 or 10.

Effects of Disclosure

A novel fluorine-containing pyrazole compound having a heterocyclic structure at the 1-position, a trifluoromethyl group at the 4-position, and specific substituents at the 3-position and the 5-position, and a method capable of easily producing the fluorine-containing pyrazole compound, can be provided.

DETAILED DESCRIPTION (Fluorine-Containing Pyrazole Compound)

The fluorine-containing pyrazole compound of the present disclosure is represented by the following general formula (1):

[Formula 4]

(1)

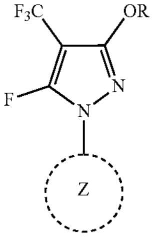

wherein in formula (1) above,

R represents a hydrocarbon group having 1 to 12 carbon atoms, and a ring Z represents an aromatic heterocyclic ring containing at least one heteroatom selected from the group consisting of a nitrogen atom, an oxygen atom, and a sulfur atom.

The fluorine-containing pyrazole compound of the present disclosure has a group of aromatic heterocyclic ring Z on the 1-position of a pyrazole ring, and specific substituents (—OR, —$CF_3$, —F) on the 3-position, 4-position, and 5-position of the pyrazole ring, and thereby it can have an excellent effect from the viewpoint of structural expandability. In particular, desired biological activities (for example, hormone or enzyme inhibitory activity, bactericidal activity, insecticidal activity, and herbicidal activity) can be expected. In particular, examples of the bactericidal activity include the bactericidal activity of bacteria having a harmful effect on agricultural products such as the human body and rice. The aromatic heterocyclic ring Z located on the 1-position of the pyrazole ring contains at least one atom selected from the group consisting of a nitrogen atom, an oxygen atom, and a sulfur atom as a heteroatom, and the ring Z may or may not further have a substituent. The ring Z can impart desired properties to the fluorine-containing pyrazole compound depending on the number and type of heteroatoms, a size of the ring, the number of ring atoms, the number of π electrons constituting the ring Z, as well as the number, type and presence or absence of substituents or the like. Moreover, the substituents on the 3- and 5-positions of the pyrazole ring being different groups (—OR and —F) facilitates derivatization into an asymmetric structure by elimination or reaction of these groups, which can be expected to be used as an intermediate. More specifically, a fluorine-containing pyrazole compound being reacted under acidic conditions to modify —OR enables to form a derivative. Moreover, a fluorine-containing pyrazole compound being reacted under basic conditions to modify —F enables to form a derivative. The fluorine-containing pyrazole compound of one embodiment is useful in the field of electronic materials such as organic semiconductors and liquid crystals.

R is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group and the like. The chain hydrocarbon group is not particularly limited as long as the total number of carbon atoms is 1 to 12 and may be a branched chain hydrocarbon group or a chain hydrocarbon group having no branch. The aromatic hydrocarbon group is not particularly limited as long as the total number of carbon atoms is 5 to 12 and may even be an aromatic hydrocarbon group having a substituent or an aromatic hydrocarbon group having no substituent. Moreover, the aromatic hydrocarbon group may have a condensed polycyclic structure. The alicyclic hydrocarbon group is not particularly limited as long as the total number of carbon atoms is 3 to 12 and may even be an alicyclic hydrocarbon group having a substituent or an alicyclic hydrocarbon group having no substituent. Further, the alicyclic hydrocarbon group may have a bridged ring structure.

Examples of the chain hydrocarbon group include alkyl groups such as a methyl group, an ethyl group, an n-propyl group, an i-propyl group, a n-butyl group, an i-butyl group, a sec-butyl group, a t-butyl group, a pentyl group, a hexyl group, a heptyl group, an octyl group, a nonyl group, a decyl group, an undecyl group, a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group, a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group, a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group, a norbornyl group and the like.

R is preferably an alkyl group having 1 to 10 carbon atoms. R being an alkyl group having 1 to 10 carbon atoms can easily prepare the fluoroisobutylene derivative of the general formula (2) and the fluoroisobutane derivative of the general formula (4), which are raw materials of the fluorine-containing pyrazole compound.

The ring Z represents an aromatic heterocyclic ring containing at least one heteroatom selected from the group consisting of a nitrogen atom, an oxygen atom, and a sulfur atom. The ring Z is not particularly limited as long as it is an aromatic heterocyclic ring containing at least one type of atom of a nitrogen atom, an oxygen atom, and a sulfur atom that are heteroatoms as a ring atom. The ring Z includes one type, two types, or three types of heteroatoms. Further, the ring Z may have a monocyclic structure or a condensed ring structure.

Typically, the number of π electrons constituting the ring Z is 4n+2 (n is a positive integer), but the number of π electrons is preferably 6, 10 or 14. More preferably the ring Z includes at least a nitrogen atom as a heteroatom and the number of π electrons constituting the ring Z is 6 or 10. When the ring Z has the aforementioned structure, polarity and planarity of the fluorine-containing pyrazole compound are controlled, so that dynamics are improved and more effective biological activity can be imparted.

More specifically, a group composed of ring Z includes a furyl group, a thienyl group, a pyrrolyl group, a pyridyl group, an oxazolyl group, an isooxazolyl group, a thiazolyl group, an isothiazolyl group, a benzofuranyl group, a benzothienyl group, an indolyl group, an isoindolyl group, a benzothiazolyl group, a benzoxazolyl group, a pyrazinyl group, a pyrimidinyl group, a pyridazinyl group, a quinolinyl group, an isoquinolinyl group, a naphthyridinyl group, pyridopyrimidinyl group, pyridopyrazinyl group, triazolyl group, benzotriazolyl group, flopyridyl group, a flopyrimidinyl group, a thienopyridyl group, a thienopyridinyl group, a pyrrolo pyrrolyl group, a chlorotrifluoromethylpyridyl group and the like.

Among these groups, the group composed of ring Z is preferably a 2-benzothiazolyl group, a 2-pyridyl group, a 3-pyridyl group, or a 3-chloro-5-trifluoromethyl-2-pyridyl group. A substituent may or may not be further bonded to the ring atom in the group composed of ring Z. Examples of the substituent bonded to the ring atom include a halogen atom, a hydrocarbon group having 1 to 10 carbon atoms, $—C_nF_{2n+1}$ where n is an integer of 1 to 10, a nitro group, a boronic acid group, $—OA^1$ and $—SO_mA^1$ where m is an integer of 0 to 3, $—NA^1A^2$, $—COOA^1$ or $—CONA^1A^2$ where $A^1$ and $A^2$ each independently represent a hydrogen atom or a hydrocarbon group having 1 to 10 carbon atoms.

(Method for Producing Fluorine-Containing Pyrazole Compound)

The method for producing a fluorine-containing pyrazole compound according to one embodiment includes (a) reacting a fluoroisobutylene derivative represented by the following general formula (2) with a compound represented by the following general formula (3) or a salt thereof to obtain a fluorine-containing pyrazole compound represented by the following general formula (1):

[Formula 5]

(2)

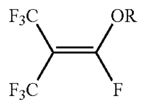

(3)

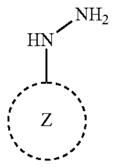

(1)

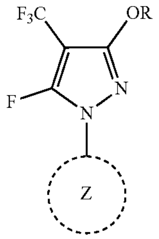

wherein in formulae (1) to (3) above,

R represents a hydrocarbon group having 1 to 12 carbon atoms, and a ring Z represents an aromatic heterocyclic ring containing at least one heteroatom selected from the group consisting of a nitrogen atom, an oxygen atom, and a sulfur atom.

Preferably, the above (a) obtaining the fluorine-containing pyrazole compound is preferably carried out in the presence of a fluoride ion scavenger. The fluoroisobutylene derivative represented by the general formula (2) is preferably reacted with the compound represented by the general formula (3) or a salt thereof in the presence of the fluoride ion scavenger. The fluoride ion scavenger is not particularly limited as long as it is a substance having a function of capturing fluorine ions, and examples of the fluoride ion scavenger include lithium, sodium, magnesium, potassium, calcium, tetramethylammonium, trifluoroacetic acid, heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonylimide, tetraphenylboric acid, tetrakis[3,5-bis(trifluoromethyl)phenyl]boric acid, tetrakis(pentafluorophenyl)borate. It is conceivable that a cation derived from the fluoride ion scavenger captures fluorine ions free from the fluoroisobutylene derivative represented by the general formula (2) during reaction, allowing a salt having low solubility to precipitate in an organic solvent to promote a reaction, and enabling to obtain the fluorine-containing pyrazole compound represented by the general formula (1) above in a high yield.

In the aforementioned general formulae (1) and (3) of step (a) above, the ring Z may have a monocyclic structure or a condensed ring structure. The number of π electrons constituting the ring Z is preferably 6, 10 or 14, and more preferably the ring Z includes at least a nitrogen atom as a heteroatom and the number of π electrons constituting the ring Z is 6 or 10. Moreover, R in the general formulae (1) and (2) above preferably represents an alkyl group having 1 to 10 carbon atoms. A substituent may or may not be further bonded to the ring atom in the group composed of ring Z. Examples of the substituent bonded to the ring atom include a halogen atom, a hydrocarbon group having 1 to 10 carbon atoms, $—C_nF_{2n+1}$ where n is an integer of 1 to 10, a nitro group, a boronic acid group, $—OA^1$ and $—SO_mA^1$ where m is an integer of 0 to 3, $—NA^1A^2$, $—COOA^1$ or $—CONA^1A^2$ where $A^1$ and $A^2$ each independently represent a hydrogen atom or a hydrocarbon group having 1 to 10 carbon atoms.

A reaction of (a) above between the fluoroisobutylene derivative represented by the general formula (2) and the compound represented by the general formula (3) is represented by the following reaction formula (A).

[Formula 6]

(A)

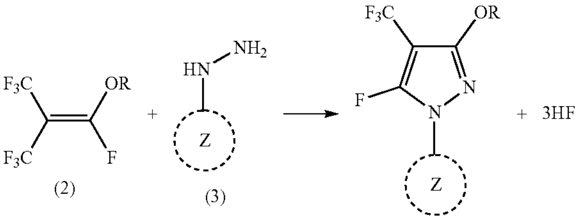

(2) (3) (1)

In the reaction formula (A), the compound of the general formula (3) each may be in a form of salt. The form of salt includes, for example, a form of at least one moiety of the amino moiety ($—NH_2$) and the imino moiety ($=NH$) constituting the amidino group of the compound of the general formula (3), being cationized to ($—NH_3^+$) and ($=NH_2^+$) to form a salt with the counterion. The counterion is not particularly limited as long as it is a monovalent anion, and includes, for example, halide ions such as $F^-$, $Cl^-$, $Br^-$, and $I^-$.

In the method for producing the fluorine-containing pyrazole compound according to one embodiment, for example, reaction (a) above can be carried out in one step in the presence of the hydrogen halide scavenger. Therefore, the fluorine-containing pyrazole compound of the general formula (1) above can be easily obtained. Incidentally, the reaction of (a) above forms a cyclic pyrazole structure between the fluoroisobutylene derivative and the amidino group of the compound of the general formula (3). At the 1-position of the pyrazole structure, a group derived from the ring structure Z of the compound of the general formula (3) is located. Further, —OR, $CF_3$, and F derived from the fluoroisobutylene derivative are located at the 3-position, 4-position, and 5-position of the pyrazole structure, respectively.

The hydrogen halide scavenger is a substance having a function of capturing hydrogen fluoride (HF) formed from a hydrogen atom derived from the amidino group in the compound of the general formula (3) and a fluorine atom derived from the fluoroisobutylene derivative of the general formula (2) in reaction formula (A) above. The hydrogen halide scavenger that is sodium hydroxide, potassium hydroxide, calcium hydroxide, sodium carbonate, potassium carbonate, sodium fluoride and potassium fluoride, and organic nitrogen derivatives such as pyridine, triethylamine, diisopropylethylamine, diazabicyclo nonane and diazabicyclo undecene, methyl triazabicyclodecene, diazabicyclo octane, and phosphazene base, can be used.

A reaction temperature upon reaction of (a) above is preferably 0 to 100° C., more preferably 5 to 50° C., and still more preferably 10 to 20° C. A reaction time upon reaction of (a) above is preferably 1 to 48 hours, more preferably 2 to 36 hours, and still more preferably 4 to 24 hours.

A solvent used in reaction (a) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water, and a water-insoluble solvent such as dichloromethane, toluene and diethyl ether. Moreover, as a catalyst for reaction of (a) above, quaternary ammonium halides such as benzyltriethylammonium chloride, a quaternary phosphonium halide, and crown ether, can be used.

The method for producing a fluorine-containing pyrazole compound according to another embodiment includes (b) reacting a fluoroisobutane derivative represented by the following general formula (4) with a compound represented by the following general formula (3) or a salt thereof to obtain a fluorine-containing pyrazole compound represented by the following general formula (1):

[Formula 7]

(4)

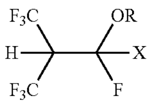

(3)

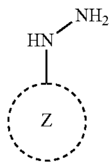

(1)

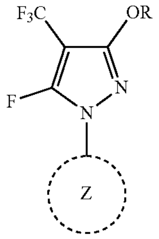

wherein in formulae (1) (3), and (4)

R represents a hydrocarbon group having 1 to 12 carbon atoms,

X represents a halogen atom, —$OA^1$, —$SO_mA^1$ where m is an integer of 0 to 3, or —$NA^1A^2$, $A^1$ and $A^2$ each independently represent a hydrogen atom or a hydrocarbon group having 1 to 10 carbon atoms, and a ring Z represents an aromatic heterocyclic ring containing at least one heteroatom selected from the group consisting of a nitrogen atom, an oxygen atom, and a sulfur atom.

Preferably, the above (b) obtaining the fluorine-containing pyrazole compound is preferably carried out in the presence of a fluoride ion scavenger. The fluoroisobutane derivative represented by the general formula (4) is preferably reacted with the compound represented by the general formula (3) or a salt thereof in the presence of a fluoride ion scavenger. The fluoride ion scavenger is not particularly limited as long as it is a substance having a function of capturing fluorine ions, and examples of the fluoride ion scavenger include lithium, sodium, magnesium, potassium, calcium, tetramethylammonium, trifluoroacetic acid, and heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonylimide, tetraphenylboric acid, tetrakis[3,5-bis(trifluoromethyl)phenyl]boric acid, tetrakis(pentafluorophenyl)borate. It is conceivable that a cation derived from the fluoride ion scavenger captures a fluorine ion free from the fluoroisobutane derivative represented by the general formula (4) during reaction, allowing a salt having low solubility to precipitate in an organic solvent to promote a reaction, and enabling to obtain the fluorine-containing pyrazole compound represented by the general formula (1) in a high yield.

In the general formulae (1) and (3) of step (b) above, the ring Z may have a monocyclic structure or a condensed ring structure. The number of π electrons constituting the ring Z is preferably 6, 10 or 14, and more preferably the ring Z includes at least a nitrogen atom as a heteroatom, and the number of π electrons constituting the ring Z is 6 or 10. Moreover, R in the aforementioned general formulae (1) and (4) preferably represents an alkyl group having 1 to 10 carbon atoms. A substituent may or may not be further bonded to the ring atom in the group composed of ring Z. Examples of the substituent bonded to the ring atom include a halogen atom, a hydrocarbon group having 1 to 10 carbon atoms, —$C_nF_{2n+1}$ where n is an integer of 1 to 10, a nitro group, a boronic acid group, —$OA^1$ and —$SO_mA^1$ where m is an integer of 0 to 3, —$NA^1A^2$, —$COOA^1$ or —$CONA^1A^2$ where $A^1$ and $A^2$ each independently represent a hydrogen atom or a hydrocarbon group having 1 to 10 carbon atoms.

The reaction of (b) above between the fluoroisobutane derivative represented by the general formula (4) and the compound represented by the general formula (3) is represented by the following reaction formula (B).

[Formula 8]

(B)

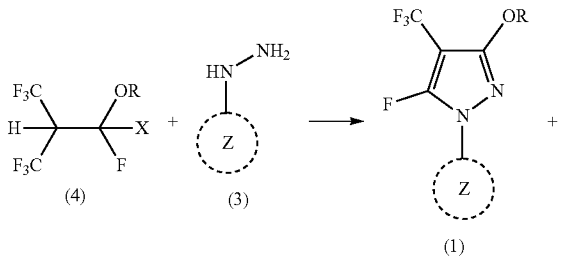

3HF + HX

In the aforementioned reaction formula (B), the compounds of the general formula (3) each may be in a form of salt. The form of salt includes, for example, a form of at least one moiety of the amino moiety (—$NH_2$) and the imino moiety (=NH) constituting the amidino group of the compound of the general formula (3), being cationized to (—$NH_3^+$) and (=$NH_2^+$) to form a salt with the counterion. The counterion is not particularly limited as long as it is a monovalent anion, and includes, for example, halide ions such as $F^-$, $Cl^-$, $Br^-$, and $I^-$.

Examples of the halogen atom that is X include F, Cl, Br, and I. $A^1$ included in —$OA^1$ and —$SO_mA^1$ where m is an integer of 0 to 3, that are X, represents a hydrogen atom or a hydrocarbon group having 1 to 10 carbon atoms. $A^1$ and $A^2$ included in —$NA^1A^2$, which are X, each independently represent a hydrogen atom or a hydrocarbon group having 1 to 10 carbon atoms. $A^1$ and $A^2$ representing a hydrocarbon group having 1 to 10 carbon atoms, can be, for example, hydrocarbon groups having 1 to 10 carbon atoms in the above R.

In the method for producing the fluorine-containing pyrazole compound according to the other embodiment, for example, the reaction of (B) above can be carried out in one step. Therefore, the fluorine-containing pyrazole compound of the general formula (1) above can be easily obtained. Incidentally, the reaction of (b) above forms a cyclic pyrazole structure between the fluoroisobutane derivative (4) and the amidino group of the compound of the general formula (3). At the 1-position of the pyrazole structure, a group derived from the ring structure Z of the compound of the general formula (3) is located. Further, —OR, $CF_3$, and F derived from the fluoroisobutane derivative are located at the 3-position, 4-position, and 5-position of the pyrazole structure, respectively.

A reaction temperature upon reaction of (b) above is preferably 0 to 100° C., more preferably 5 to 50° C., and still more preferably 10 to 20° C. A reaction time upon reaction of (b) above is preferably 1 to 48 hours, more preferably 2 to 36 hours, and still more preferably 4 to 24 hours. In the reaction of (b) above, the same hydrogen halide scavenger as (a) above can be used.

A solvent used in reaction (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for reaction (b) above, quaternary ammonium halides such as benzyltriethylammonium chloride, a quaternary phosphonium halide, crown ether and the like, can be used.

Although the embodiments of the present disclosure have been described above, the present disclosure is not limited to the aforementioned embodiments, and includes all aspects included in the concept and claims of the present disclosure and can be modified within the scope of the present disclosure.

EXAMPLES

Next, in order to further clarify the effect of the present disclosure, Examples will be described, but the present disclosure is not limited to these Examples.

Example 1

Production of 5-fluoro-3-methoxy-1-(2-benzothiazolyl)-4-trifluoromethylpyrazole Under ice-water cooling, 5 g (30 mmol) of 2-hydrazinobenzthiazole, 29 g (91 mmol) of potassium bis(trifluoromethanesulfonyl)imide, and 8.3 g (39 mmol) of 1,3,3,3-tetrafluoro-1-methoxy-2-trifluoromethyl-1-propene were added to 100 g of THF (tetrahydrofuran) to obtain a THF solution 1. Subsequently, 60 g of a THF solution 2 containing 37 g (120 mmol) of tertiary butyliminotripyrrolidinophosphorane was added dropwise to the THF solution 1 such that the internal temperature did not exceed 10° C. The mixed solution of THF solutions 1 and 2 were raised to room temperature and held for about 72 hours to produce 5-fluoro-3-methoxy-1-(2-benzothiazolyl)-4-trifluoromethylpyrazole. Then, a silica gel column purification was performed using a mixed solvent of hexane-ethyl acetate=7:3 (volume ratio) to isolate 950 mg of 5-fluoro-3-methoxy-1-(2-benzothiazolyl)-4-trifluoromethylpyrazole (molecular weight of 317.26) represented by the following formula (C). The isolated yield of 5-fluoro-3-methoxy-1-(2-benzothiazolyl)-4-trifluoromethylpyrazole was 10%.

[Formula 9]

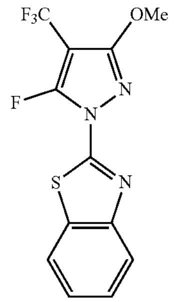

(C)

The analysis results of the target product obtained are as follows.

Mass Spectrum (APCl, m/z): 317 ($[M]^+$)

$^1H$-NMR (300 MHz, $CDCl_3$) δ ppm: 7.97 (d, 1H), 7.84 (d, 1H), 7.51 (dt, 1H), 7.40 (dt, 1H), 4.07 (s, 3H)

$^{19}F$-NMR (300 MHz, $C_6F_6$) δ ppm: −58.9 (d, 3F), −114.2 (dd, 1F)

Example 2

Production of 5-fluoro-3-methoxy-1-(2-pyridyl)-4-trifluoromethylpyrazole

Under ice-water cooling, 5 g (46 mmol) of 2-hydrazinopyridine and 13 g (60 mmol) of 1,3,3,3-tetrafluoro-1-methoxy-2-trifluoromethyl-1-propene were added to 100 g of THF (tetrahydrofuran) to obtain a THF solution 1. Subsequently, 40 g of a THF solution 2 containing 27 g (180 mmol) of diazabicycloundecene was added dropwise to the THF solution 1 such that the internal temperature did not exceed 10° C. The mixed solution of THF solutions 1 and 2 was raised to room temperature and held for about 72 hours to produce 5-fluoro-3-methoxy-1-(2-pyridyl)-4-trifluoromethylpyrazole. Then, a silica gel column purification was performed using a mixed solvent of hexane-ethyl acetate=7:3 (volume ratio) to isolate 360 mg of 5-fluoro-3-methoxy-1-(2-pyridyl)-4-trifluoromethylpyrazole (molecular weight of 261.18) represented by the following formula (D). The isolated yield of 5-fluoro-3-methoxy-1-(2-pyridyl)-4-trifluoromethylpyrazole was 3%.

[Formula 10]

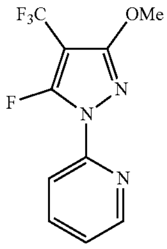

(D)

The analysis results of the target product obtained are as follows.

Mass Spectrum (APCl, m/z): 261 ($[M]^+$)

$^1$H-NMR (300 MHz, $CDCl_3$) δ ppm: 8.32 (d, 1H), 7.67 (dt, 1H), 7.50 (d, 1H), 7.09 (m, 1H), 3.86 (s, 3H)

$^{19}$F-NMR (300 MHz, $C_6F_6$) δ ppm: −58.1 (d, 3F), −115.7 (dd, 1F)

Example 3

Production of 5-fluoro-3-methoxy-1-(3-pyridyl)-4-trifluoromethylpyrazole

Under ice-water cooling, 5 g (34 mmol) of 3-hydrazinopyridine hydrochloride and 9.5 g (45 mmol) of 1,3,3,3-tetrafluoro-1-methoxy-2-trifluoromethyl-1-propene were added to 100 g of THF (tetrahydrofuran) to obtain a THF solution 1. Subsequently, 40 g of a THF solution 2 containing 27 g (180 mmol) of diazabicycloundecene was added dropwise to the THF solution 1 such that the internal temperature did not exceed 10° C. The mixed solution of THF solutions 1 and 2 was raised to room temperature and held for about 72 hours to produce 5-fluoro-3-methoxy-1-(3-pyridyl)-4-trifluoromethylpyrazole. Then, a silica gel column purification was performed using a mixed solvent of hexane-ethyl acetate=7:3 (volume ratio) to isolate 621 mg of 5-fluoro-3-methoxy-1-(3-pyridyl)-4-trifluoromethylpyrazole (molecular weight of 261.18) represented by the following formula (E). The isolated yield of 5-fluoro-3-methoxy-1-(3-pyridyl)-4-trifluoromethylpyrazole was 7%.

[Formula 11]

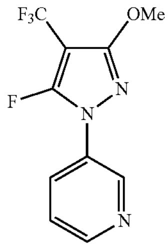

(E)

The analysis results of the target product obtained are as follows.

Mass Spectrum (APCl, m/z): 261 ($[M]^+$)

$^1$H-NMR (300 MHz, $CDCl_3$) δ ppm: 8.92 (s, 1H), 8.61 (d, 1H), 7.93 (m, 1H), 7.44 (m, 1H), 4.02 (s, 3H)

$^{19}$F-NMR (300 MHz, $C_6F_6$) δ ppm: −58.5 (d, 3F), −119.7 (dd, 1F)

Example 4

Production of 5-fluoro-3-methoxy-1-(2-benzothiazolyl)-4-trifluoromethylpyrazole by using 1,1,1,3,3-pentafluoro-3-methoxy-2-(trifluoromethyl)-propane Instead of 1,3,3,3-tetrafluoro-1-methoxy-2-(trifluoromethyl)-1-propene of Example 1

Under ice-water cooling, 5 g (30 mmol) of 2-hydrazinobenzthiazole, 39 g (120 mmol) of potassium bis(trifluoromethanesulfonyl)imide, and 9.1 g (39 mmol) of 1,1,1,3,3-pentafluoro-3-methoxy-2-(trifluoromethyl)-propane were added to 100 g of THF (tetrahydrofuran) to obtain a THF solution 1. Subsequently, 80 g of a THF solution 2 containing 49 g (160 mmol) of tertiary butyliminotripyrrolidinophosphorane was added dropwise to the THF solution 1 such that the internal temperature did not exceed 10° C. The mixed solution of THF solutions 1 and 2 was raised to room temperature and held for about 72 hours. The analysis results of the obtained compound were the same as those of the product of Example 1.

Example 5

Production of 5-fluoro-3-methoxy-1-(2-pyridyl)-4-trifluoromethylpyrazole by Using 1,1,1,3,3-pentafluoro-3-methoxy-2-(trifluoromethyl)-propane Instead of 1,3,3,3-tetrafluoro-1-methoxy-2-(trifluoromethyl)-1-propene of Example 2

Under ice-water cooling, 5 g (46 mmol) of 2-hydrazinopyridine and 14 g (60 mmol) of 1,1,1,3,3-pentafluoro-3-methoxy-2-(trifluoromethyl)-propane were added to 100 g of THF (tetrahydrofuran) to obtain a THF solution 1. Subsequently, 80 g of a THF solution 2 containing 36 g (240 mmol) of diazabicycloundecene was added dropwise to the THF solution 1 such that the internal temperature did not exceed 10° C. The mixed solution of THF solutions 1 and 2 was raised to room temperature and held for about 72 hours. The analysis results of the obtained compound were the same as those of the product of Example 2.

Example 6

Production of 5-fluoro-3-methoxy-1-(3-pyridyl)-4-trifluoromethylpyrazole by Using 1,1,1,3,3-pentafluoro-3-methoxy-2-(trifluoromethyl)-propane Instead of 1,3,3,3-tetrafluoro-1-methoxy-2-(trifluoromethyl)-1-propene of Example 3

Under ice-water cooling, 5 g (34 mmol) of 3-hydrazinopyridine hydrochloride and 10 g (45 mmol) of 1,1,1,3,3-pentafluoro-3-methoxy-2-(trifluoromethyl)-propane were added to 100 g of THF (tetrahydrofuran) to obtain a THF solution 1. Subsequently, 60 g of a THF solution 2 containing 34 g (220 mmol) of diazabicycloundecene was added dropwise to the THF solution 1 such that the internal temperature did not exceed 10° C. The mixed solution of THF solutions 1 and 2 was raised to room temperature and held for about 72 hours. The analysis results of the obtained compound were the same as those of the product of Example 3.

Example 7

Production of 1-(3-chloro-5-trifluoromethyl-2-pyridyl)-5-fluoro-3-methoxy-4-trifluoromethylpyrazole 2.3 g (7.2 mmol) of potassium bis(trifluoromethanesulfonyl)imide, 0.6 g (2.8 mmol) of 1,3,3,3-tetrafluoro-1- methoxy-2-trifluoromethyl-1-propene, and 1.1 g (7.2 mmol) of 1,8-diazabicyclo[5.4.0]-7-undecene were added into a solution obtained by dissolving 0.5 g (2.4 mmol) of 3-chloro-2-hydrazinyl-5-(trifluoromethyl)pyridine in 15 ml of tetrahydrofuran, and the mixture was stirred at room temperature for 17.6 hours to obtain a reaction solution. After that, the reaction solution was purified by a column to obtain 0.1 g (0.2 mmol) of 1-(3-chloro-5-trifluoromethyl-2-pyridyl)-5-fluoro-3-methoxy-4-trifluoromethylpyrazole (molecular weight: 363.62), represented by the following formula (F). The isolated yield of 1-(3-chloro-5-trifluoromethyl-2-pyridyl)-5-fluoro-3-methoxy-4-trifluoromethylpyrazole was 28.0%.

[Formula 12]

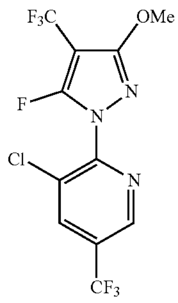

(F)

The analysis results of the target product obtained are as follows.

Mass Spectrum (APCI, m/z): 363.6 ([M]$^+$)

$^1$H-NMR (400 MHz, $CDCl_3$) δ ppm: 8.78 (dd, J=2.2, 1.1 Hz, 1H), 8.20 (d, J=1.8 Hz, 1H), 4.01 (s, 3H)

Test Example

Evaluation Test for Rice Blast

The 5-fluoro-3-methoxy-1-(2-pyridyl)-4-trifluoromethylpyrazole prepared in Example 2 was dissolved in acetone to prepare an acetone solution containing 100,000 ppm of 5-fluoro-3-methoxy-1-(2-pyridyl)-4-trifluoromethylpyrazole. Next, sterilized water was added to 1 ml of this acetone solution to make 50 ml, to prepare a test solution having a concentration of 2,000 ppm. 1,000 μl of the test solution having a concentration of 2,000 ppm was added dropwise to a separately prepared oatmeal culture medium and was air-dried. Subsequently, an 8 mm rice blast disc was placed such that flora contacted a treated surface of the oatmeal culture medium. Then, the oatmeal culture medium was allowed to stand still in a thermostatic room at 25° C. for 7 days, and an elongation length of hyphae was then investigated. The preventive value calculated according to the expression below was 80, and the 5-fluoro-3-methoxy-1-(2-pyridyl)-4-trifluoromethylpyrazole prepared in Example 2 was confirmed to have an excellent bactericidal activity.

Preventive value={(average of elongation lengths of hyphae without treatment−average of elongation lengths of hyphae with treatment)/(average of elongation lengths of hyphae without treatment}×100

In the expression above, "without treatment" means that only sterilized water was added dropwise to the culture medium as the test solution.

"With treatment" means that a test solution that had been diluted and adjusted to a set concentration was added dropwise to the culture medium as the test solution.

The invention claimed is:

1. A fluorine-containing pyrazole compound represented by the following general formula (1):

[Formula 1]

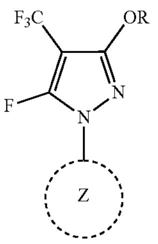

(1)

wherein R represents an unsubstituted chain hydrocarbon group having 1 to 12 carbon atoms; and a ring Z represents an aromatic heterocyclic ring containing at least one heteroatom selected from the group consisting of a nitrogen atom, an oxygen atom, and a sulfur atom.

2. The fluorine-containing pyrazole compound according to claim 1, wherein a number of π electrons constituting the ring Z is 6, 10, or 14.

3. The fluorine-containing pyrazole compound according to claim 1, wherein the ring Z contains at least a nitrogen atom as the heteroatom, and a number of π electrons constituting the ring Z is 6 or 10.

4. A method for producing a fluorine-containing pyrazole compound represented by the following general formula (1), comprising reacting a fluoroisobutylene derivative represented by the following general formula (2) with a compound represented by the following general formula (3), or a salt thereof, to obtain a fluorine-containing pyrazole compound represented by the following general formula (1):

[Formula 2]

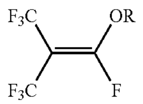

(2)

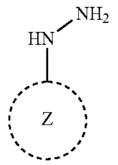

(3)

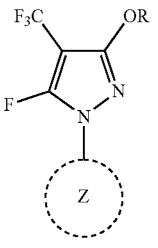

(1)

wherein

R represents an unsubstituted chain hydrocarbon group having 1 to 12 carbon atoms, and a ring Z represents an aromatic heterocyclic ring containing at least one heteroatom selected from the group consisting of a nitrogen atom, an oxygen atom, and a sulfur atom.

5. A method for producing a fluorine-containing pyrazole compound represented by the following general formula (1), comprising reacting a fluoroisobutane derivative represented by the following general formula (4) with a compound represented by the following general formula (3), or a salt thereof, to obtain a fluorine-containing pyrazole compound represented by the following general formula (1):

[Formula 3]

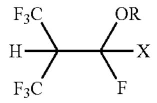

(4)

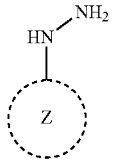

(3)

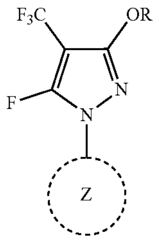

(1)

wherein

R represents an unsubstituted chain hydrocarbon group having 1 to 12 carbon atoms, X represents a halogen atom, —$OA^1$, —$SO_mA^1$, wherein m is an integer of 0 to 3, or —$NA^1A^2$, $A^1$ and $A^2$ each independently represent a hydrogen atom or a hydrocarbon group having 1 to 10 carbon atoms, and a ring Z represents an aromatic heterocyclic ring containing at least one heteroatom selected from the group consisting of a nitrogen atom, an oxygen atom, and a sulfur atom.

6. The method for producing a fluorine-containing pyrazole compound according to claim 4, wherein the step of obtaining a fluorine-containing pyrazole compound is carried out in the presence of a fluoride ion scavenger.

7. The method for producing a fluorine-containing pyrazole compound according to claim 4, wherein a number of π electrons constituting the ring Z is 6, 10, or 14.

8. The method for producing a fluorine-containing pyrazole compound according to claim 4, wherein the ring Z contains at least a nitrogen atom as the heteroatom, and a number of π electrons constituting the ring Z is 6 or 10.

9. The method for producing a fluorine-containing pyrazole compound according to claim 5, wherein the step of obtaining a fluorine-containing pyrazole compound is carried out in the presence of a fluoride ion scavenger.

10. The method for producing a fluorine-containing pyrazole compound according to claim 5, wherein a number of π electrons constituting the ring Z is 6, 10, or 14.

11. The method for producing a fluorine-containing pyrazole compound according to claim 5, wherein the ring Z contains at least a nitrogen atom as the heteroatom, and a number of π electrons constituting the ring Z is 6 or 10.

* * * * *